United States Patent [19]

Thompson

[11] 4,325,193
[45] Apr. 20, 1982

[54] SHELF ARRANGEMENT FOR FREEZE DRYING APPARATUS

[75] Inventor: Marc J. Thompson, New Paltz, N.Y.

[73] Assignee: The Virtis Company, Inc.

[21] Appl. No.: 210,714

[22] Filed: Nov. 26, 1980

[51] Int. Cl.³ .............................................. F26B 13/30
[52] U.S. Cl. ........................................................ 34/92
[58] Field of Search ........................................ 34/5, 92

[56] References Cited

U.S. PATENT DOCUMENTS

| 3,286,366 | 11/1966 | Seligman | 34/5 |
| 3,461,953 | 8/1969 | Costello et al. | 34/92 |
| 3,537,233 | 11/1970 | Costello et al. | 34/92 |
| 4,177,577 | 12/1979 | Bird | 34/92 |

Primary Examiner—John J. Camby
Attorney, Agent, or Firm—Kirkland & Ellis

[57] ABSTRACT

A shelf arrangement is disposed within the vacuum drying chamber of a freeze dryer. The shelf arrangement has a plurality of vertically-movable shelves, flanges of which are positioned within vertically disposed, elongated slots. The slots are located in side plates, which plates maintain upper and lower bracket assemblies in spaced-apart relation. Certain of the slots are provided with stop means for rendering certain of the shelves vertically immovable. Elevating means are provided for raising and lowering the movable shelves.

4 Claims, 6 Drawing Figures

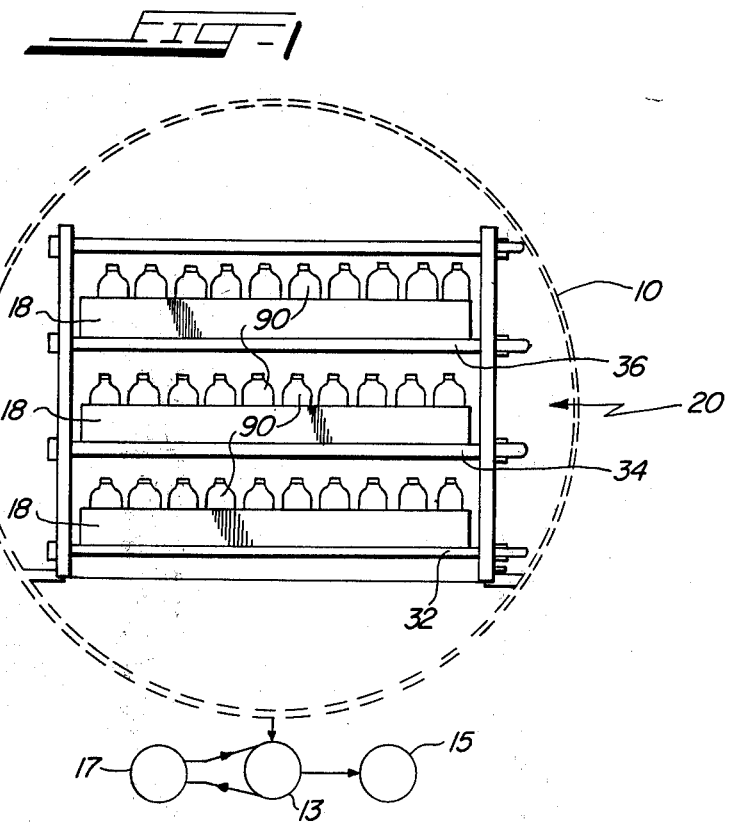
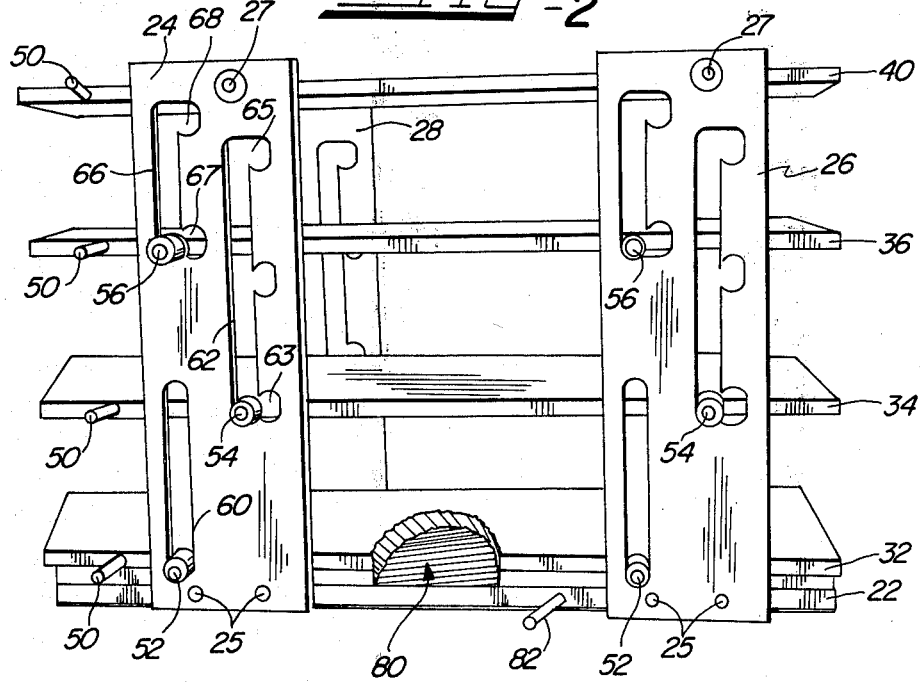

SHELF ARRANGEMENT FOR FREEZE DRYING APPARATUS

BACKGROUND OF THE INVENTION

1. Field of the Invention

The present invention relates to freeze drying apparatus, and more particularly, to shelf structures for utilization in freeze drying apparatus.

2. Description of the Prior Art

The method of freeze drying biological specimens and other materials such as medicine and food products by sublimation of ice in a vacuum has been known for over fifty years. It was not until shortly before World War II, however, that the true commercial potential of laboratory freeze dryers and the process of sublimation were recognized. Particularly, during World War II, substantial development was made in the equipment and techniques for the purposes of supplying medical products to the armed forces. Since that time, increased interest by food processors as well as pharmaceutical manufacturers has resulted in further development of freeze drying equipment. Thus, freeze drying has found application not only in the laboratory for various scientific purposes, but commercially as well.

Basically, the process of freeze drying involves the lowering of the temperature of a moisture-containing item or sample until it is in a completely solid state, i.e., until it is frozen. The sample is then maintained in the area of a very low absolute pressure or high vacuum and subjected to a controlled heat input. Application of the heat to the product at a controlled rate results in the water content of the frozen sample being sublimated (i.e., converted directly from a solid to a gas without passing through the liquid state). The gaseous water vapor is then effectively removed from the system by being refrozen onto a refrigerated condenser thereby protecting the vacuum pump oil from contamination by water vapor. The refrozen moisture can be removed from the condenser when the drying process is completed. The condenser can be located in the same chamber as the shelf assembly or in a separate condensation chamber. Representative examples of some prior art freeze drying apparatus are shown in U.S. Pat. No. 3,795,986—Sutherland et al., U.S. Pat. No. 3,950,963—Sutherland, U.S. Pat. No. 3,286,366—Seligman, U.S. Pat. No. 3,271,874—Oppenheimer and U.S. Pat. No. 4,173,078—Bird, et al.

In the types of freeze drying apparatus which are used for commercial purposes, such as freeze drying medicines, the material to be dried is usually placed in glass vials or containers supported on a shelf arrangement within the drying chamber. The vials typically have stoppers partially inserted in the open ends thereof, but the stoppers have slots which allow the moisture to escape from the interior of the vial during the freeze drying process. However, once the drying process has been completed, the vials must be closed before the drying chamber is open to prevent contamination when moisture-containing atmosphere enters the drying chamber. Consequently, various types of shelf arrangements have been provided which allow the shelves to be raised one against the other so that the vials are squeezed "accordion style" between the shelves driving the stoppers into the vials thereby sealing the vials. In other prior art freeze dryers, each shelf remains stationary but the pan or receptacle in which the vials are placed is positioned over an inflatable bladder. A plate large enough to cover all of the vials in one pan is placed on the tops of the stoppers. When the freeze drying sequence is completed, the bladder is inflated, thereby causing the pan to be moved vertically until the top surface of the plate strikes the bottom surface of the next higher shelf. Continued inflation of the bladder forces the stoppers into the necked-down portion of the vials and results in a sealing of the vials.

Prior art shelf arrangements have experienced various problems such as high frictional forces due to misalignment of the sliding surfaces thereof which have restricted proper operation of the prior art shelf arrangements. Those prior art arrangements utilizing multiple bladders are expensive in relation to the usable freeze drying volume within the drying chamber.

BRIEF DESCRIPTION OF THE INVENTION

The present invention is used in freeze drying apparatus of the type including a sealable, vacuum-tight drying chamber, a refrigerated condenser for condensing and freezing moisture removed from items being dried in the drying chamber, a vacuum pump connected to the drying chamber for evacuating the air from the drying chamber, and a cooling system for cooling the condenser. Such structure is well known in the art as disclosed in U.S. Pat. Nos. 3,795,986—Sutherland et al., 3,950,963—Sutherland, 3,286-366—Seligman, 3,271,874—Oppenheimer, and 4,173,078—Bird, et al.

The present invention is an improved shelf arrangement for use in the drying chamber of such freeze drying apparatus and comprises a rigid frame assembly having an upper plate and a lower plate and spacing members holding the upper plate and lower plate in a spaced-apart relationship. A multiplicity of elongated slots are vertically disposed in the spacing members. A multiplicity of cut-outs are provided in said slots for supporting shelf means at pre-determined elevations. Elevating means are mounted on the lower plate and are operably connected to the lowest shelf means of the multiplicity of shelf means to cause the lowest shelf means to move vertically. The elevating means, which is a fluid inflatable member, communicates through an opening with a fluid reservoir. The multiplicity of shelf means, which contain a plurality of flange means, may be positioned in one or more pre-determined locations such that inflation of the elevating means causes one or more of the multiplicity of shelf means to move vertically. Upon inflation of the elevating means, the lowest shelf means moves vertically until it, or an object resting thereon, contacts the next higher shelf means. In the event the latter-mentioned shelf means is in a travel position, it will also move upwardly. Vertical travel of the multiplicity of shelf means occurs as indicated until a shelf means which is in the locked position is contacted or until all of the multiplicity of shelf means have been moved through their range of travel. Upon deflation of the elevating means, the lowest shelf means is caused to move vertically downward to its original position and each higher shelf means descends until the respective flange means engage the bottoms of the slots into which they are placed.

The invention also incorporates cut-outs or locking means for selectively locking certain of the shelf means in a vertically elevated position so that the remaining shelfs can be reoriented with respect to one another between the upper and lower plate.

Thus, it is a principal object of the present invention to provide a shelf arrangement for freeze drying apparatus which utilizes a fluid inflatable bladder to elevate the the shelves in the apparatus.

Yet another object of the present invention is to provide means for adjusting the vertical travel of each shelf so that the position of the shelves can be varied.

A further object of the present invention is to provide a progressive shelf mechanism for a shelf arrangement and freeze drying apparatus that allows one or more upper shelves to be latched in an elevated out of the way position so that the remaining shelves can be redistributed positionally to allow larger items to be supported by the shelves.

These and other objects, advantages, and features of the present invention shall hearinafter appear, and for the purpose of illustration, but not for limitation, an exemplary embodiment of the present invention is illustrated in the accompanying drawings and described in the accompanying detailed description.

DESCRIPTION OF THE DRAWINGS

FIG. 1 is a front elevational view of a shelf arrangement in accordance with the present invention.

FIG. 2 is a side perspective partially fragmentary view of a shelf arrangement in accordance with the present membrane.

DETAILED DESCRIPTION OF THE PREFERRED EMBODIMENT

Figure 3:
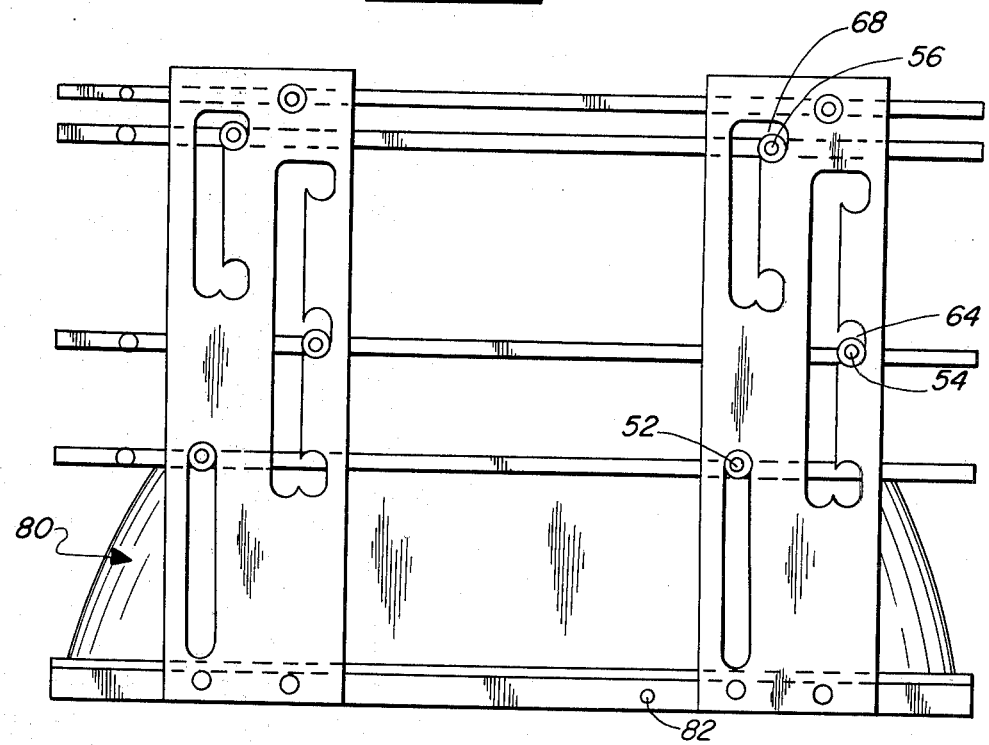
FIG. 3 is a side elevational view of a shelf arrangement in accordance with the present invention showing the fully inflated elevating means.

With respect to FIG. 1, a shelf assembly 20 is positioned in a drying chamber 10 (shown in dotted lines) of a freeze dryer. Graphically represented in FIG. 1 is a condenser 13 associated with the drying chamber 10 that communicates with the drying chamber 10, a vacuum pump 15 that evacuates the air and moisture from the drying chamber 10, and a cooling system 17 for refrigerating the condenser to refreeze the moisture removed from the items being dried in the drying chamber 10. The condenser 13 may take the form of a condensation chamber separate from the drying chamber 10, or a condenser element positioned within drying chamber 10, both of which structures are conventional in the art. Positioned on shelves 32, 34 and 36 are pans 18 which contain vials 90. The vials 90 hold material which is to be freeze dried.

As shown in FIG. 2, the improved shelf assembly 20 comprises an upper bracket assembly 40 and a lower bracket assembly 22 which are held in a spaced relationship essentially parallel to one another by spacer elements in the form of side plates 24, 26, 28 and 30 (the plate 30 not being shown in FIG. 2). The lower most end of the side plates may be attached to the drying chamber 10 by means of bolts (not shown) passing through holes 25. The upper most ends of the side plates are attached to the upper bracket assembly 40 by means of bolts 27; both of said attachments being known in the art.

The side plates 24, 26, 28 and 30 each contain a multiplicity of vertically elongated slots, with the slots in one side plate being constructed substantially identical to those in the remaining side plates. For example, side plate 24 contains slots 60, 62 and 66. Slot 62 is constructed with cut-outs 63, 64 and 65; slot 66 is constructed with cut outs 67 and 68. Slot 60 has no cut-outs.

Positioned within the slot 60 are flanges 52 connected to a lowest shelf means 32. The flanges 52, which are preferrably cylindrically shaped, may be coated or covered with Teflon or a similar friction reducing material. The shelf means 32 may include an opening 50 for communication through flexible tubing (not shown) with a reservoir containing heat exchanging fluids (not shown). Likewise, positioned within the slot 62 are flanges 54 attached to intermediate shelf means 34. The shelf means 34 may also be constructed with the opening 50. Positioned within the slot 66 are flanges 56 attached to upper shelf means 36. The shelf means 36 may also be constructed with opening 50 as may be the upper bracket assembly 40. The shelf means 32, 34 and 36 and the upper bracket assembly 40 may be a hollow assembly with serpentine-configured tubing disposed therein (not shown) for the purpose of flowing heat exchange fluids therethrough as is known in the art.

The lower bracket assembly 22 is constructed with elevating means 80. In the present invention, the elevating means 80 comprises a fluid inflatable bladder which communicates through an opening 82 in the lower bracket assembly 22 with a fluid reservoir (not shown). The opening 82 may be placed at any location in the lower bracket assembly 22. The lower bracket assembly 22, because it is not attached to the side plates 24, 26, 28 and 30, may be removed from the shelf assembly 20 to facilitate replacement of the elevating means 80.

As can be seen from FIG. 2, each of the shelf means 32, 34 and 36 are free to move up and down in the slots 60, 62 and 66, respectively.

To move the shelf means up and down, the bladder 80 is inflated. When this occurs, the lowest shelf means 32 moves vertically upward in the slot 60 until the shelf means 32 moves through its full range of travel as determined by the vertical length of the slot 60 or until the shelf means 32 is unable to travel vertically as hereinafter described.

Figure 6:
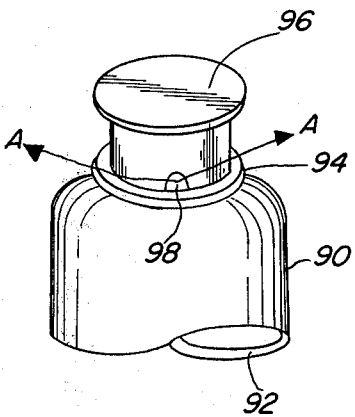
FIG. 6 is an upper perspective partially fragmentary view of a representative glass vial and stopper that would be positioned on the shelves of the shelf arrangement shown in FIGS. 1-5.

Ordinarily, during the freeze drying process, a plurality of glass vials 90 are positioned on one or more of the shelf means 32, 34 and 36 (see FIG. 1). With reference to FIG. 6, the vials 90 may comprise a hollow glass body 92 having a necked-down opening 94 at the upper end thereof into which a stopper 96 is partially inserted. Stopper 96 has at least one slot 98 along the edge thereof which allows moisture to escape from the material within vial 90 which is being dried in the freeze drier. The removal of moisture is graphically illustrated by the arrows A in FIG. 6 which represents water vapor being removed from the material within vial 90 by the freeze drying process.

Once the material in all of the plurality of vials on all of the shelf means has been freeze dried, it is necessary to drive the stoppers 96 down into the vials 90 so that the material within the vials is not contaminated by moisture or other material in the atmosphere when the drying chamber door is open. Thus, by moving the shelf means 32, 34 and 36 upwardly, the plurality of vials on all of the shelves are squeezed between the shelves, thereby pushing the stoppers into the vials sealing them from further moisture contamination. This procedure occurs when the bladder 80 within the lower bracket assembly 22 is inflated. (FIG. 3 depicts the bladder 80 in the fully inflated position.) Upon inflation, the lowest shelf means 32 is moved vertically upward until the stoppers 96 have contacted the undersurface of the shelf means 34. Upon such contact, the shelf means 34 is caused to rise vertically upward until the stoppers 96 of the vials resting thereon contact the undersurface of the shelf means 36 and, when this occurs, the shelf 36 is moved vertically upward until the stoppers 96 of the vials resting thereon conact the undersurface of the upper bracket assembly 40. With all of the shelves so positioned, additional pressurization of the bladder 80 will cause the stoppers 96 to be driven down into the vials 90.

In certain instances, it may be desirable to position vials 90 only on the lowest shelf means 32. Accordingly, before the freeze drying process commences the flange 54 of the shelf means 34 is pre-set in the cut-out 63. As will be appreciated, in such position the shelf means 34 is vertically immovable and when the bladder 80 is inflated the stoppers 96 of vials resting on the shelf means 32 may be brought into contact with the undersurface of the shelf means 34. Additional pressurization of the bladder 80 causes the stoppers 96 to be driven into the vials 90.

Due to the positioning of the cut-outs 63, 64, 65, 67 and 68, the present invention provides for selective positioning of the shelves 34 and 36. For example, as shown in FIG. 3, the flange 54 of shelf 34 is positioned in cut-out 64. Such positioning renders the shelf means 34 vertically immovable and permits the use of taller vials on the shelf means 32 than that described in the preceding paragraph.

Figure 4:
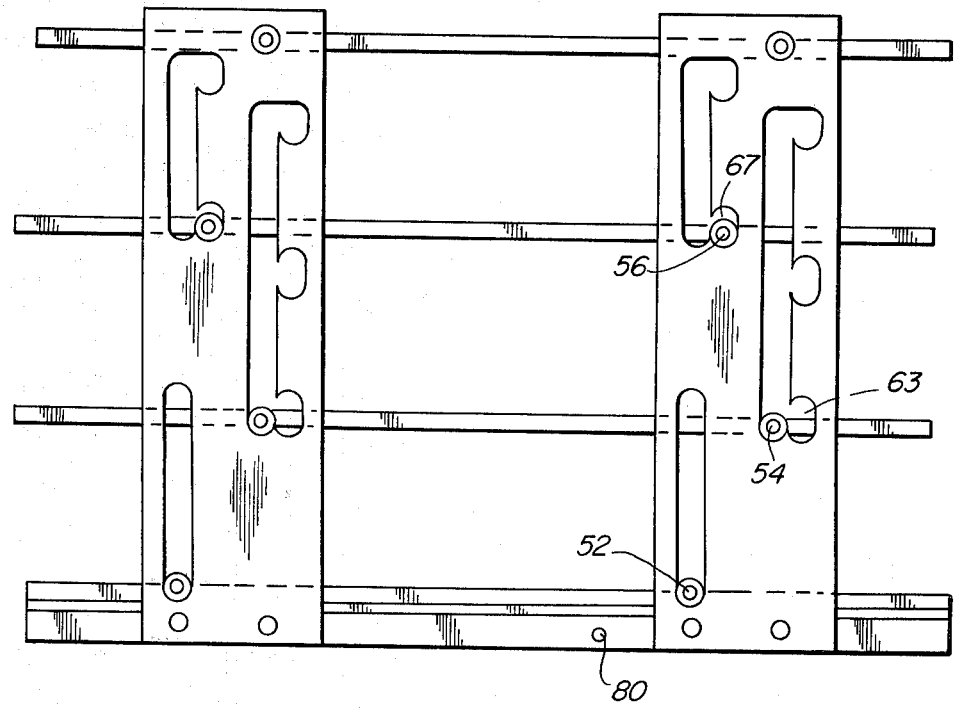
FIG. 4 is a side elevational view of a shelf arrangement in accordance with the present invention depicting shelf positions.

FIG. 4 shows the positioning of the shelf means of the present invention for the stopping of vials placed on shelves 32 and 34. Because the flange 56 of the shelf means 36 is positioned in the cut-out 67, the shelf means 36 is vertically immovable. The stoppering of vials placed on the shelfs 32 and 34 proceeds as described above.

Figure 5:
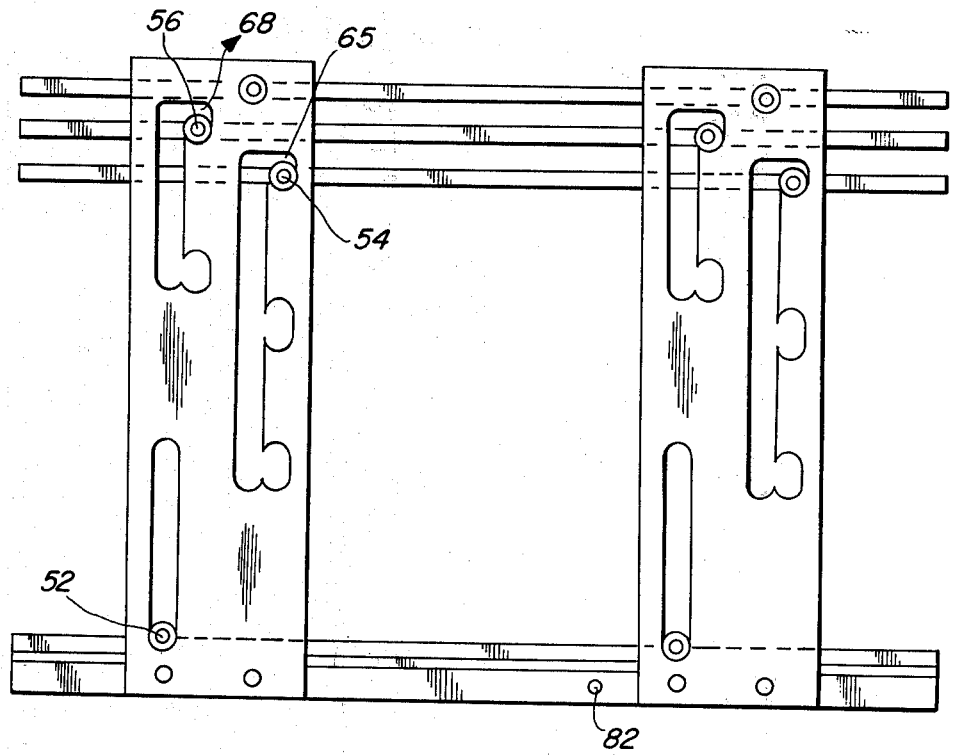
FIG. 5 is a side elevational view of a shelf arrangement in accordance with the present invention depicting shelf positions.

In certain instances, it may be desirable to use relatively tall vials as containers for freeze dried material. Accordingly, the present invention permits the positioning of the shelves 34 and 36 in upper most, locked positions. As shown in FIG. 5, the flange 54 of the shelf means 34 is positioned in cut-out 65 and the flange 56 of the shelf means 36 is positioned in cut-out 68. When so positioned, relatively large vials may be placed on the shelf means 32 and stoppered in a manner similar to that described above.

It should be apparent from the foregoing that various modifications, alterations, and changes may be made to the embodiment as illustrated and described herein without departing from the spirit and scope of the present invention as defined in the appended claims. In particular, while the invention has been described with reference to three movable shelf means, it will be appreciated that more or less shelf means may be included while still falling within the intent and scope of the invention. Likewise, while the invention has been described in conjunction with a limited number and position of cut-outs, more or less cut-outs may be utilized located at different positions in the side plates. All of these modifications are contemplated in the present incentive.

I claim:

1. In a freeze dryer of the type including a sealable vacuum-tight drying chamber, a refrigerator condenser for condensing and freezing moisture removed from items being dried in the drying chamber, a vacuum pump connected to the drying chamber for evacuating the air from the drying chamber, and a cooling system for cooling the condenser; an improved shelf arrangement for use in the drying chamber comprising:
   a rigid frame assembly having an upper bracket, and a lower bracket;
   a plurality of slotted spacing members holding said upper bracket and said lower bracket in a spaced-apart relationship;
   stop means provided in said spacing members at predetermined positions along respective slots of said spacing members;
   a plurality of shelf means for supporting items to be dried in the drying chamber;
   flange means mounted on said shelf means in suitable positions to slidably travel in said slots of said spacing members, said flange means adapted for positioning in said stop means so that the corresponding flange means of said shelf means are supported by respective ones of said stop means in predetermined positions between said upper bracket and said lower bracket; and
   an inflatable elevating means mounted on said lower bracket, said elevating means operably connectable to the lowest shelf means of said plurality of shelf means to cause said lowest shelf means to move vertically when said elevating means is inflated.

2. The apparatus according to claim 1, wherein said shelf means comprises a hollow body adapted for communication with a reservoir of heat exchange fluid.

3. The apparatus according to claim 1, wherein each of said spacing members includes a plurality of spaced-apart slots.

4. The apparatus according to claim 3, wherein the slots associated with the lowest shelf means of said plurality of shelf means have no stop means positioned between the ends of said slots.

* * * * *